(12) United States Patent
Chen

(10) Patent No.: US 11,639,876 B2
(45) Date of Patent: May 2, 2023

(54) TEMPERATURE MEASURING METHOD CAPABLE OF SWITCHING CALCULATION BASED ON DISPLACEMENT DETECTION

(71) Applicant: Hetaida Technology Co., Ltd., Dongguan (CN)

(72) Inventor: Zhenguang Chen, Dongguan (CN)

(73) Assignee: HETAIDA TECHNOLOGY CO., LTD., Dongguan (CN)

( * ) Notice: Subject to any disclaimer, the term of this patent is extended or adjusted under 35 U.S.C. 154(b) by 982 days.

(21) Appl. No.: 16/450,966

(22) Filed: Jun. 24, 2019

(65) Prior Publication Data

US 2020/0319037 A1 Oct. 8, 2020

(30) Foreign Application Priority Data

Apr. 8, 2019 (CN) .......................... 201910276964.1

(51) Int. Cl.
| | | |
|---|---|---|
| *G01J 5/02* | (2022.01) |
| *G01J 5/00* | (2022.01) |
| *G01K 13/20* | (2021.01) |
| *A61B 5/06* | (2006.01) |
| *G01K 15/00* | (2006.01) |

(52) U.S. Cl.
CPC .............. *G01K 13/223* (2021.01); *A61B 5/067* (2013.01); *G01J 5/0025* (2013.01); *G01J 5/026* (2013.01); *G01K 13/20* (2021.01); *G01K 15/00* (2013.01)

(58) Field of Classification Search
CPC ...... G01K 13/223; G01K 13/20; G01K 15/00; A61B 5/067; G01J 5/0025; G01J 5/026; G01J 5/0275
See application file for complete search history.

(56) References Cited

U.S. PATENT DOCUMENTS

| | | | | |
|---|---|---|---|---|
| 2015/0035680 A1* | 2/2015 | Li | ......................... | A61B 5/7246 340/584 |
| 2019/0388031 A1* | 12/2019 | Haber | ..................... | G01K 1/165 |

* cited by examiner

*Primary Examiner* — Christine S. Kim
(74) *Attorney, Agent, or Firm* — Leong C. Lei

(57) ABSTRACT

A temperature measuring method capable of switching calculation based on displacement detection includes a temperature measuring instrument and a displacement detecting unit. When the displacement detecting unit feeds back that the temperature measuring instrument is under an inactive state, a point calculation formula A is used to calculate and obtain a body temperature value. When the displacement detecting unit feeds back that the temperature measuring instrument is under an active state, a scanning calculation formula B is used to calculate and obtain the body temperature value.

7 Claims, 3 Drawing Sheets

TEMPERATURE MEASURING METHOD CAPABLE OF SWITCHING CALCULATION BASED ON DISPLACEMENT DETECTION

BACKGROUND OF THIS INVENTION

1. Field of this Invention

This invention relates to a body temperature measuring method and relates particularly to a temperature measuring method capable of switching calculation based on displacement detection.

2. Description of the Related Art

An infrared thermometer is operated by transforming radiant energy which is contained in the infrared ray emitted by a measured object into an electrical signal. The magnitude of the infrared radiant quantity is related to a temperature of the object. The temperature of the object can be determined based on the intensity of transformed electrical signal.

When measuring a body temperature value, it is necessary to hold the infrared thermometer and remain immobile. Any motion caused during the measurement will affect the measuring result. Therefore, the operator is demanded strictly and it limits the operation range of the infrared thermometer.

Therefore, in this invention, the applicant has elaborately researched and developed a new technical solution to solve the above problems.

SUMMARY OF THIS INVENTION

Therefore, this invention focuses on the deficiencies of the prior art to provide the main object which is a temperature measuring method capable of switching calculation based on displacement detection and that can obtain a more precise body temperature value, facilitate the temperature measuring operation, reduce the operation requirement of temperature measuring, and increase the practicality.

In order to achieve the above object, this invention adopts the following technical solutions:

A temperature measuring method capable of switching calculation based on displacement detection comprising a temperature measuring instrument and a displacement detecting unit for detecting a change of position of the temperature measuring instrument. When the displacement detecting unit feeds back that the temperature measuring instrument is under an inactive state, a point calculation formula A is used to calculate and obtain a body temperature value. When the displacement detecting unit feeds back that the temperature measuring instrument is under an active state, a scanning calculation formula B is used to calculate and obtain the body temperature value.

Preferably, the displacement detecting unit is disposed in the temperature measuring instrument.

Preferably, the temperature measuring instrument includes an arithmetic unit. The point calculation formula A and the scanning calculation formula B are arithmetic formulas stored in the arithmetic unit respectively.

Preferably, the temperature measuring instrument includes an infrared temperature measuring unit. During measuring a temperature, the infrared temperature measuring unit obtains an infrared signal C.

When the temperature measuring instrument is under the inactive state, the infrared signal C is combined with the point calculation formula A to obtain a body temperature value D1.

When the temperature measuring instrument is under the active state, the infrared signal C is combined with the scanning calculation formula B to obtain a body temperature value D2.

Preferably, the displacement detecting unit includes a linear transducer and/or an angular velocity transducer.

Preferably, the displacement detecting unit includes an acceleration transducer and/or a gyroscope.

Preferably, a motion trajectory distance and/or angle detected by the displacement detecting unit is determined when the displacement detecting unit feeds back that the temperature measuring instrument is under the active state. When the detected motion trajectory distance and/or angle fit in a setting range, a scanning test is considered as tallying with conditions. The scanning calculation formula B is applied to calculate and obtain the body temperature value, otherwise, the scanning test is considered as unavailable.

Preferably, when the motion trajectory distance and/or angle detected by the displacement detecting unit is larger than a setting value, the scanning test is considered as tallying with conditions. The scanning calculation formula B is applied to calculate and obtain the body temperature value, otherwise, the scanning test is considered as unavailable.

Preferably, an alarm signal is sent out for warning when the scanning test is unavailable.

Compared with the prior art, this invention has obvious advantages and beneficial effects. Specifically, from the above technical solutions, it mainly takes an advantage of the displacement detecting unit to detect the change of position of the temperature measuring instrument. When the displacement detecting unit feeds back that the temperature measuring instrument is under the inactive state, the point calculation formula A is used to calculate and obtain the body temperature value. When the displacement detecting unit feeds back that the temperature measuring instrument is under the active state, the scanning calculation formula B is used to calculate and obtain the body temperature value, whereby the more precise body temperature value is obtained. Simultaneously, the temperature measuring operation is facilitated to be simple and easy. The operation requirement of temperature measuring is reduced and the practicality is high.

DETAILED DESCRIPTION OF THE PREFERRED EMBODIMENTS

Figure 1:
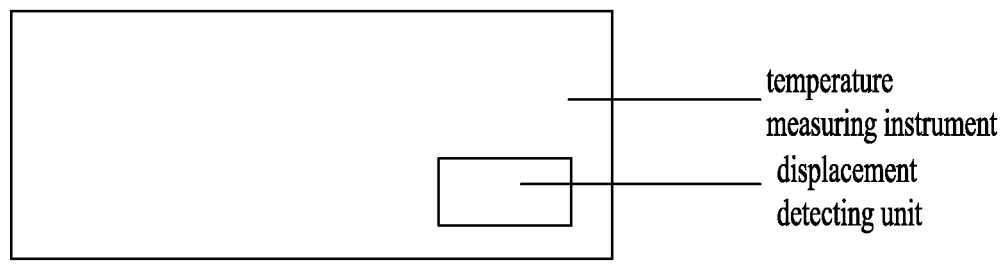
FIG. 1 is a schematic view showing temperature measuring instrument adopted in the present invention to carry out a temperature measuring method capable of switching calculation based on displacement detection according to the present invention.
Figure 2:
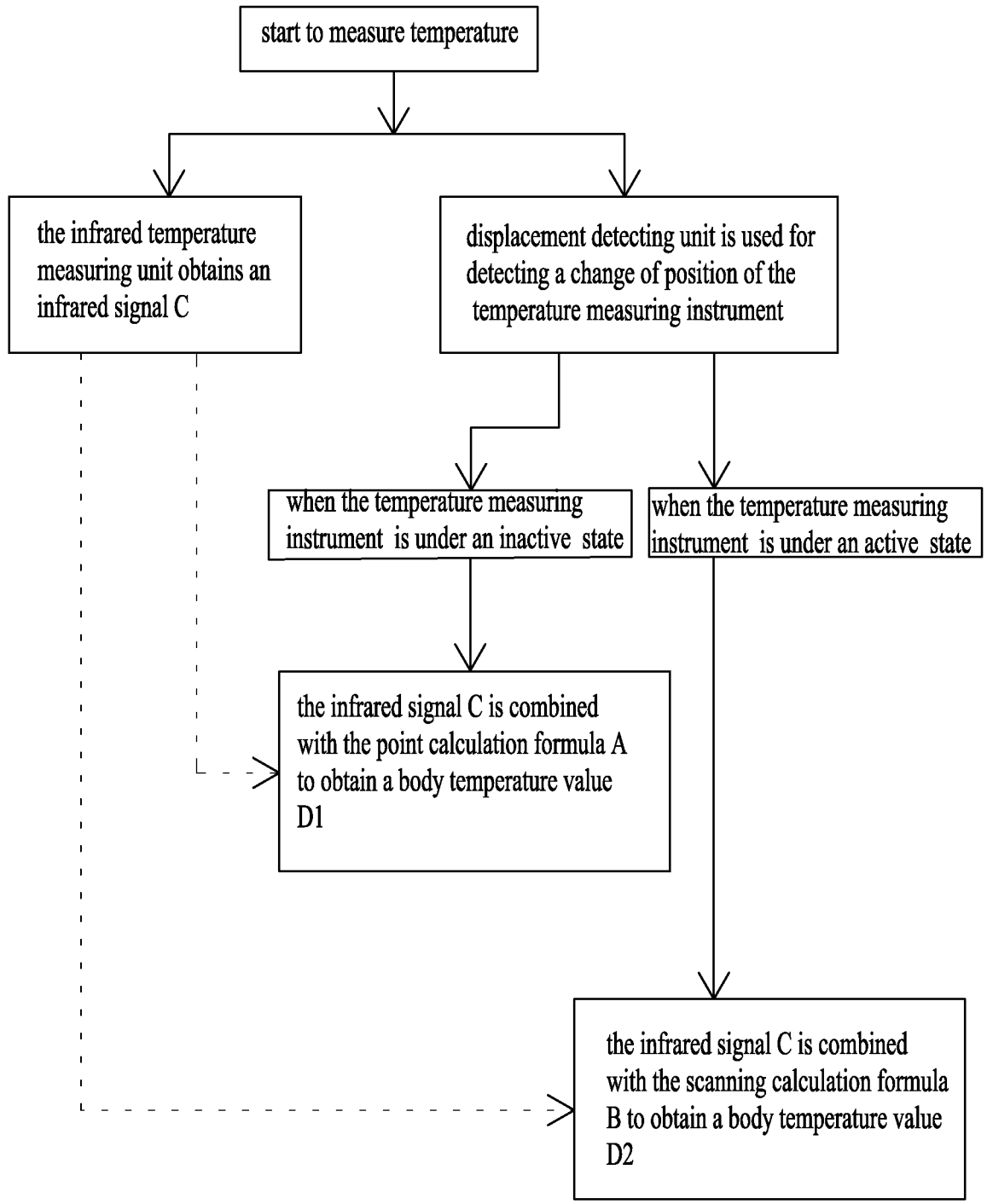
FIG. 2 is a flow chart illustrating a method according to the present invention.
Figure 3:
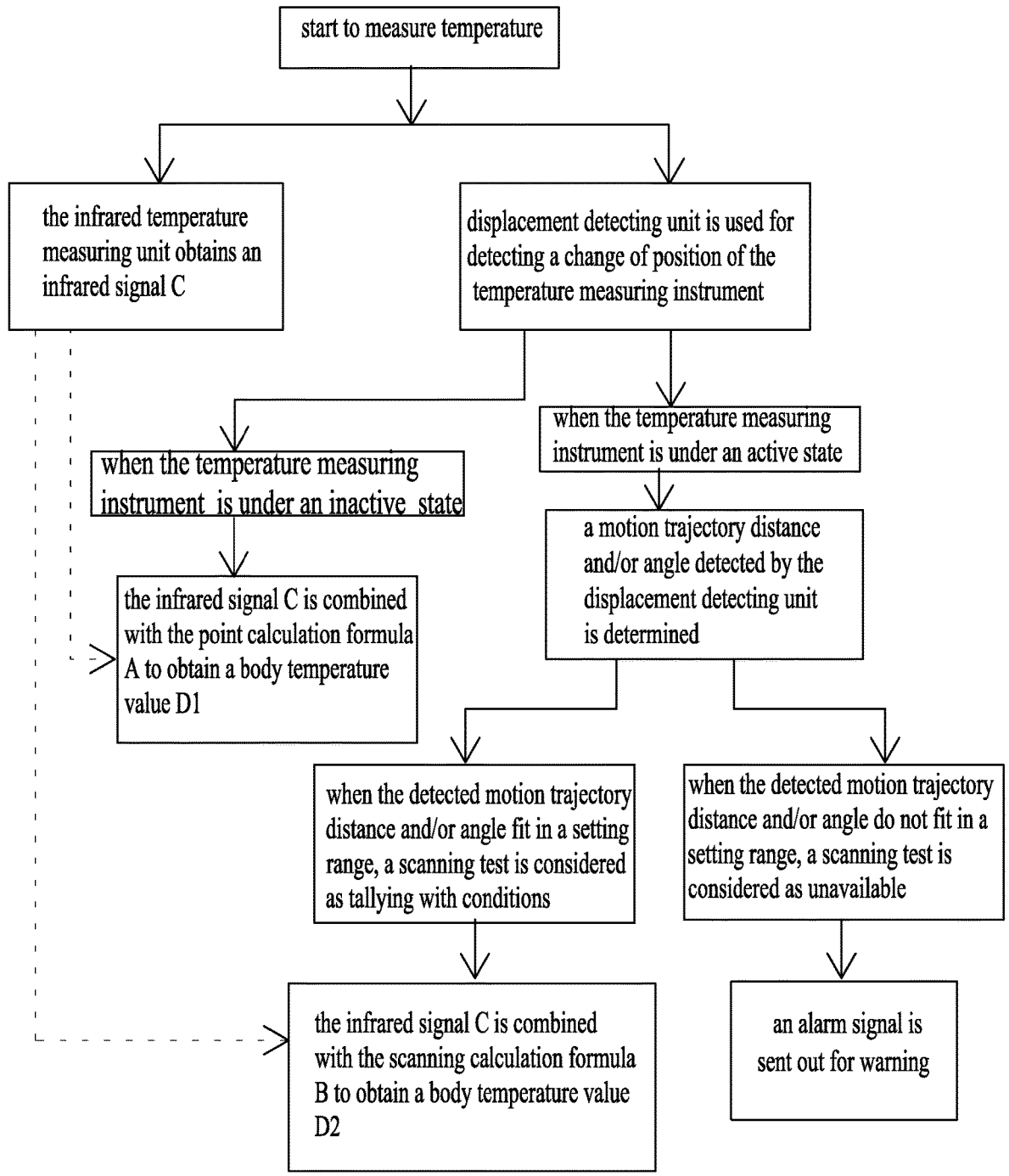
FIG. 3 is another flow chart illustrating a method according to the present invention.

Referring to FIGS. 1-3, a temperature measuring method capable of switching calculation based on displacement detection includes a temperature measuring instrument and a displacement detecting unit for detecting a change of position of the temperature measuring instrument. When the displacement detecting unit feeds back that the temperature measuring instrument is under an inactive state, a point calculation formula A is used to calculate and obtain a body temperature value. When the displacement detecting unit feeds back that the temperature measuring instrument is under an active state, a scanning calculation formula B is used to calculate and obtain the body temperature value.

Generally, the displacement detecting unit is disposed in the temperature measuring instrument. The temperature measuring instrument includes an arithmetic unit where arithmetic formulas, namely the point calculation formula A and the scanning calculation formula B, are stored respectively. The temperature measuring instrument includes an infrared temperature measuring unit which obtains an infrared signal C during measuring a temperature. When the displacement detecting unit feeds back that the temperature measuring instrument is under the inactive state, the infrared signal C is combined with the point calculation formula A to obtain a body temperature value D1. When the displacement detecting unit feeds back that the temperature measuring instrument is under the active state, the infrared signal C is combined with the scanning calculation formula B to obtain a body temperature value D2.

Specifically, the displacement detecting unit can be any device which is capable of detecting displacement. It can include, but not limited to, a linear transducer and/or an angular velocity transducer. The linear transducer can be, but not limited to, an acceleration transducer. The angular velocity transducer can be, but not limited to, a gyroscope.

When the displacement detecting unit feeds back that the temperature measuring instrument is under the active state, a motion trajectory distance and/or angle detected by the displacement detecting unit is determined. When the detected motion trajectory distance and/or angle fit in a setting range, a scanning test is considered as tallying with conditions. The scanning calculation formula B is applied to calculate and obtain the body temperature value, otherwise, the scanning test is considered as unavailable. In this embodiment, the setting range refers to a setting value. For example, when the motion trajectory distance and/or angle detected by the displacement detecting unit is larger than the setting value, the scanning test is considered as tallying with conditions. The scanning calculation formula B is applied to calculate and obtain the body temperature value, otherwise, the scanning test is considered as unavailable and an alarm signal is sent out for warning.

The main design point of this invention is to have support from the displacement detecting unit to detect the change of position of the temperature measuring instrument. When the displacement detecting unit feeds back that the temperature measuring instrument is under the inactive state, the point calculation formula A is used to calculate and obtain the body temperature value. When the displacement detecting unit feeds back that the temperature measuring instrument is under the active state, the scanning calculation formula B is used to calculate and obtain the body temperature value. Hence, the more precise body temperature value is obtained. Meanwhile, the temperature measuring operation is facilitated to be simple and easy. The operation requirement of temperature measuring is reduced and the practicality is high.

While the embodiment of this invention is shown and described above, it is understood that the embodiment is not intended to limit the technical scope of this invention. Moreover, it is understood that further detailed revisions, equivalent variations, and modifications may be made without departing from the scope of this invention.

What is claimed is:

1. A temperature measuring method capable of switching calculation based on displacement detection, comprising a temperature measuring instrument and a displacement detecting unit for detecting a change of position of said temperature measuring instrument, when said displacement detecting unit feeds back that said temperature measuring instrument is under an inactive state, a point calculation formula A is used to calculate and obtain a body temperature value, when said displacement detecting unit feeds back that said temperature measuring instrument is under an active state, said body temperature value is calculated and obtained by using a scanning calculation formula B, wherein the point calculation formula A represents a first arithmetic formula and the point calculation formula B represents a second arithmetic formula, both first and second arithmetic formulas being loaded in the temperature measuring instrument,
   wherein said temperature measuring instrument includes an infrared temperature measuring unit, during measuring a temperature, said infrared temperature measuring unit obtaining an infrared signal C,
   said infrared signal C is applicable to the first arithmetic formula of said point calculation formula A to calculate and obtain a body temperature value D1 when said displacement detecting unit feeds back that said temperature measuring instrument is under said inactive state, and
   said infrared signal C is applied to the second arithmetic formula of said scanning calculation formula B to calculate and obtain a body temperature value D2 when said displacement detecting unit feeds back that said temperature measuring instrument is under said active state, wherein a motion trajectory distance and/or angle detected by said displacement detecting unit is determined when said displacement detecting unit feeds back that said temperature measuring instrument is under said active state, and when said detected motion trajectory distance and/or angle fit in a setting range, said scanning calculation formula B is applied, in combination with said infrared signal C, to calculate and obtain said body temperature value.

2. The temperature measuring method according to claim 1, wherein said displacement detecting unit is disposed in said temperature measuring instrument.

3. The temperature measuring method according to claim 1, wherein said temperature measuring instrument includes an arithmetic unit, said point calculation formula A and said scanning calculation formula B being arithmetic formulas stored in said arithmetic unit respectively.

4. The temperature measuring method according to claim 1, wherein said displacement detecting unit includes a linear transducer and/or an angular velocity transducer.

5. The temperature measuring method according to claim 1, wherein said displacement detecting unit includes an acceleration transducer and/or a gyroscope.

6. The temperature measuring method according to claim 1, wherein when said motion trajectory distance and/or angle detected by said displacement detecting unit is larger than a setting value, said scanning calculation formula B is applied to calculate and obtain said body temperature value.

7. The temperature measuring method according to claim 1, wherein an alarm signal is sent out for warning when said detected motion trajectory distance and/or angle is outside the setting range.

* * * * *